(12) United States Patent
Sugaya

(10) Patent No.: US 10,687,713 B2
(45) Date of Patent: *Jun. 23, 2020

(54) DIAGNOSTIC APPARATUS

(71) Applicant: OPTiM Corporation, Saga (JP)

(72) Inventor: Shunji Sugaya, Tokyo (JP)

(73) Assignee: OPTIM CORPORATION, Saga-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/540,065

(22) PCT Filed: Aug. 5, 2016

(86) PCT No.: PCT/JP2016/073122
§ 371 (c)(1),
(2) Date: Jun. 27, 2018

(87) PCT Pub. No.: WO2018/025404
PCT Pub. Date: Feb. 8, 2018

(65) Prior Publication Data
US 2019/0159681 A1    May 30, 2019

(51) Int. Cl.
*A61B 5/01* (2006.01)
*G06T 7/70* (2017.01)
*A01K 29/00* (2006.01)
*A61B 5/00* (2006.01)
*G06K 9/00* (2006.01)
(Continued)

(52) U.S. Cl.
CPC .............. *A61B 5/015* (2013.01); *A01K 29/00* (2013.01); *A61B 5/0077* (2013.01); *A61B 5/7246* (2013.01); *A61B 5/7282* (2013.01); *A61B 5/7485* (2013.01); *G06K 9/00362* (2013.01); *G06T 7/0014* (2013.01); *G06T 7/70* (2017.01); *H04N 5/33* (2013.01); *A61B 2503/40* (2013.01); *A61B 2576/00* (2013.01); *G06T 2207/10004* (2013.01); *G06T 2207/10048* (2013.01)

(58) Field of Classification Search
None
See application file for complete search history.

(56) References Cited

U.S. PATENT DOCUMENTS

2012/0307046 A1* 12/2012 Lundberg ............... G01J 5/0022
348/135
2015/0302241 A1* 10/2015 Eineren ................... A01J 5/007
382/110

FOREIGN PATENT DOCUMENTS

WO    WO 2014/083433 A2 *  6/2014  ......... G06K 9/00362
WO      WO2014083433    *  6/2014  ......... G06K 9/00362

OTHER PUBLICATIONS

"Infrared thermographic analysis of body surface temperature in healthy cattle" Internet <URL: http://www.naro.affrc.go.jp/project/results/laboratory/niah/2013/niah13_s23.html>.

* cited by examiner

*Primary Examiner* — Dakshesh D Parikh
(74) *Attorney, Agent, or Firm* — Lex IP Meister, PLLC

(57) ABSTRACT

A diagnostic system 100 includes an acquiring unit 310 for acquiring a visible light image and an infrared image photographed by a camera, a first image processing unit 321 for specifying an area in the visible light image corresponding to a predetermined part of an animal photographed by the camera, a second image processing unit 322 for specifying an area in the infrared image corresponding to the area specified by the first image processing unit, and a diagnostic unit for diagnosing the animal based on a temperature at the area specified by the second image processing unit.

15 Claims, 7 Drawing Sheets

(51) Int. Cl.
*G06T 7/00* (2017.01)
*H04N 5/33* (2006.01)

| Part | Reference Temperature (°C) |
|---|---|
| Head | 30 |
| Nose | 27 |
| Shoulder | 30.5 |
| Rump | 29 |
| Limbs | 25.5 |
| Shoulder | 30 |
| Rump | 29.2 |
| Perianal | 36 |
| ... | ... |

For Animal B
For Animal A
For General Use
DB1

DIAGNOSTIC APPARATUS

TECHNICAL FIELD

The present invention relates to an apparatus for performing a diagnosis by photographing an animal.

BACKGROUND ART

There is known in the art a technique for photographing animals, such as cattle, by using thermal imaging to obtain thermographic images, and measuring body surface temperatures of different parts of the animal, so as to gain an understanding of a physical condition of the animal (Non-Patent Document 1).

PRIOR ART DOCUMENT

Non-Patent Document

Non-patent Document 1: "Infrared thermographic analysis of body surface temperature in healthy cattle" Internet <URL: https://www.naro.affrc.go.jp/project/results/laboratory/niah/2013/niah13_s23.html>

SUMMARY OF THE INVENTION

Technical Problem

Different body parts of animals such as cattle generally have different temperatures. When determining the health of a target animal by measuring a temperature of each of different parts of the target animal, it is important that such a temperature be accurately measured. However, though an outline and approximate locations of parts of cattle etc. can be specified from a thermographic image, it is difficult to specify an exact position of each part for various reasons including a distance from a camera to a subject. Consequently, accuracy of measurement of a temperature of each part is limited.

It is an object of the present invention to improve the accuracy of measuring a temperature at each part of a target animal.

Technical Solution

According to one aspect of the present invention, there is provided a diagnostic apparatus including an acquiring unit that acquires a visible light image and an infrared image photographed by a camera, a first image processing unit that specifies an area in the visible light image corresponding to a predetermined part of an animal photographed by the camera, a second image processing unit that specifies an area in the infrared image corresponding to the area specified by the first image processing unit, and a diagnostic unit that diagnoses the animal based on a temperature at the area specified by the second image processing unit.

Effects of the Invention

According to the present invention, the measurement accuracy is improved for each part of a target animal whose temperature is to be measured.

BRIEF DESCRIPTION OF THE DRAWINGS

FIG. 6 is an example of information stored in a database DB1.

DESCRIPTION OF REFERENCE NUMBERS

100: diagnostic system, 300: information processing device, 310: first acquiring unit, 320: control unit, 330: storage unit, 340: adjusting unit, 321: first image processing unit, 322: second image processing unit, 323: diagnostic unit, 350: second acquiring unit, 400: sensor, 500: cattle, 600: environment adjusting unit, 201: visible light camera, 202: infrared camera, 400: sensor

DETAILED DESCRIPTION OF THE EMBODIMENTS

Figure 1:
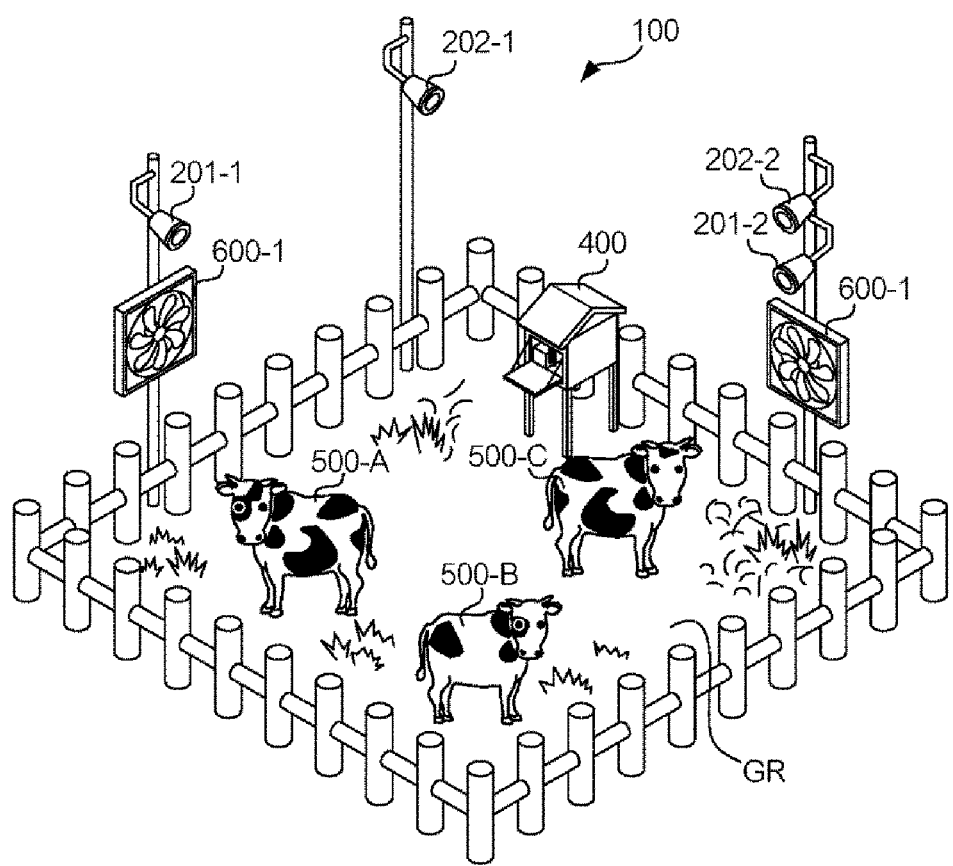
FIG. 1 is a schematic diagram of a diagnostic system 100.

FIG. 1 shows an overview of a diagnostic system 100. The diagnostic system 100 includes visible light cameras 201 (201-1 and 201-2), infrared cameras 202 (202-1 and 202-2), a sensor 400, cattle 500 (cattle 500-A, cattle 500-B, and cattle 500-C), and environment adjusting units 600 (600-1 and 600-1).

Positions or numbers of the visible light cameras 201, the infrared cameras 202, and the sensors 400 in FIG. 1 are shown merely as examples. Further, while an example of rearing and managing cattle in an outdoor grazing area GR is shown in FIG. 1, all or some of the elements of the diagnostic system 100 may be installed in an indoor space (or an outdoor space), for domestic animals managed in an indoor space.

Detailed functions of the visible light cameras 201 may be the same or different. Similarly, detailed functions of environment adjusting units 600 may be the same or different.

The sensor 400 measures information on environment of the grazing area GR, such as illumination, wind direction, wind speed, temperature, air temperature, humidity, atmospheric pressure, and the like.

The environment adjusting unit 600 is an apparatus that operates under control of an information processing apparatus 300 and changes the environment of the grazing area GR, and is, for example, an air conditioner such as a blower or a lighting device.

Figure 2:
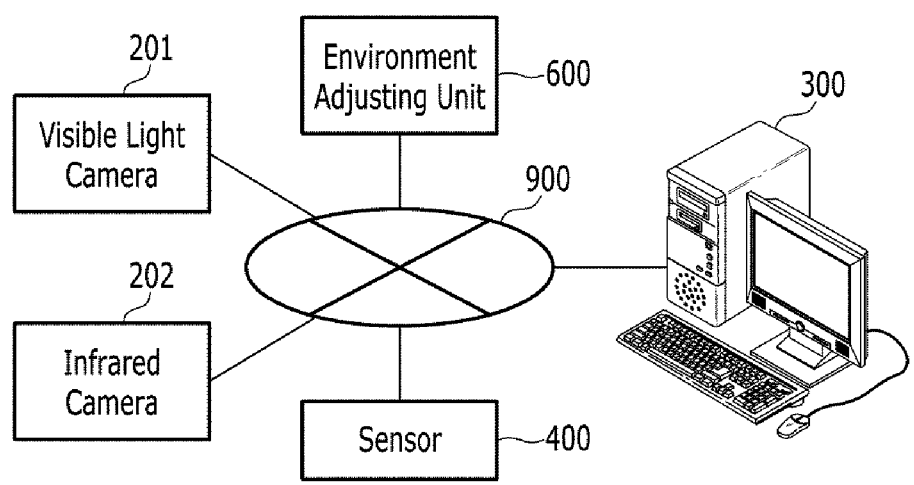
FIG. 2 is a functional diagram of a diagnostic system 100.

FIG. 2 is a functional diagram of a diagnostic system 100. The diagnostic system 100 includes a visible light camera 201, an infrared camera 202, an information processing device 300, an environment adjusting unit 600, a sensor 400, and a network 900. The information processing apparatus 300 is a general-purpose information processing apparatus such as a personal computer and is used by a user of the diagnostic system 100.

The visible light camera 201 includes an optical system such as a lens, a light detection element, an image processor, and the like, and detects light from a subject to generate image data (hereinafter referred to as "visible light image data").

The infrared camera 202 includes an optical system such as a lens, an infrared ray detecting element, an image processor, and the like, and detects an infrared ray emitted from a subject of an imaging device to generate infrared image data (thermography). The infrared image shows a representation of the temperature of each part of the subject by using color.

The generated infrared image data and visible light image data are transmitted to the information processing apparatus 300 via 900, which is a network such as a wired or wireless LAN or the internet.

Further, network 900 transmits data measured by the sensor 400 to the information processing apparatus 300. Further, a control signal is supplied from the information processing device 300 to each environment adjusting unit 600 via network 900. The control signal includes, for example, an ON/OFF timing of a power supply and a blowing rate (the number of revolutions).

In at least one of the visible light camera 201 and the infrared camera 202, an administrator of the diagnostic system 100 may perform a control of an orientation of the lens, an imaging range (zoom), a focus, or the like via a remote device (not shown). In detail, a user visually checks the image data supplied from the visible light camera 201 and the infrared camera 202 to the information processing apparatus 300 to search for and identify the subject, and transmits a control signal defining photographing conditions such as the angle of view, the focus, or the zoom from the control unit 320 to the visible light camera 201 and the infrared camera 202.

Alternatively, at least one of the visible light camera 201 and the infrared camera 202 may automatically perform adjustment of the orientation of lens, the angle of view, the focus, or the zoom, and make a determination such as designation of a transmission timing of the generated image data, according to a predetermined image recognition algorithm. In this case, the adjusted photographing conditions are transmitted to the information processing apparatus 300 together with the image data. In other words, the information processing apparatus 300 always keeps track of all operating states of the visible light cameras 201 and the infrared cameras 202.

In FIG. 2, since the infrared camera 202 and the visible light camera 201 are provided at different positions, even if the infrared camera 202 and the visible light camera 201 photograph the same subject, photographing viewpoints are different. A single infrared camera 202 and a single visible light camera 201 may form an integrated structure. In this case, the photographing viewpoints of the acquired image data are the same or substantially the same.

Timings at which the infrared image data and the visible light image data are supplied to the information processing apparatus 300 may be independent or may be synchronized. Each of the visible light image and the infrared image may be a still image or a single moving image including a plurality of still images photographed at a plurality of points in time.

Figure 3:
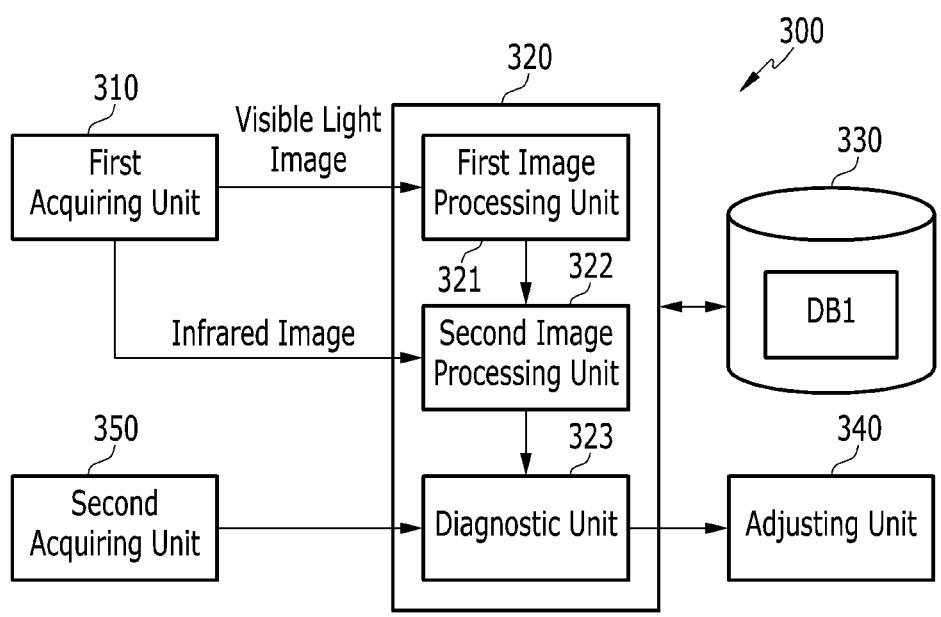
FIG. 3 is a functional diagram of an information processing apparatus 300.

FIG. 3 shows functions of an information processing apparatus 300. The information processing apparatus 300 includes a first acquiring unit 310, a control unit 320, a storage unit 330, an adjusting unit 340, and a second acquiring unit 350. The first acquiring unit 310 is implemented as a communication interface such as a LAN module and, upon acquiring a visible light image and an infrared image from a visible light camera 201 and an infrared camera 202 respectively, supplies the visible light image and the infrared image to a first image processing unit 321 and a second image processing unit 322, respectively.

Figure 4:
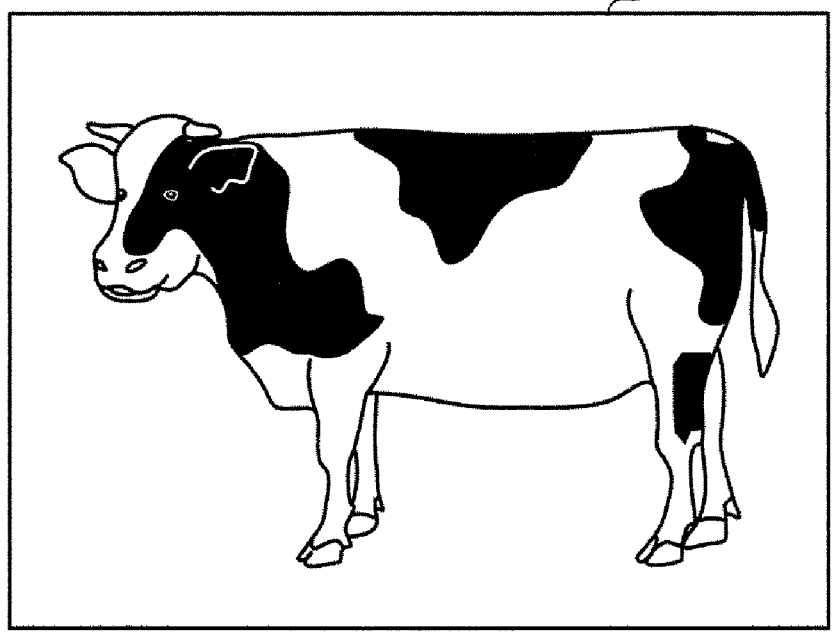
FIG. 4 shows an example of an acquired image.
Figure 4:
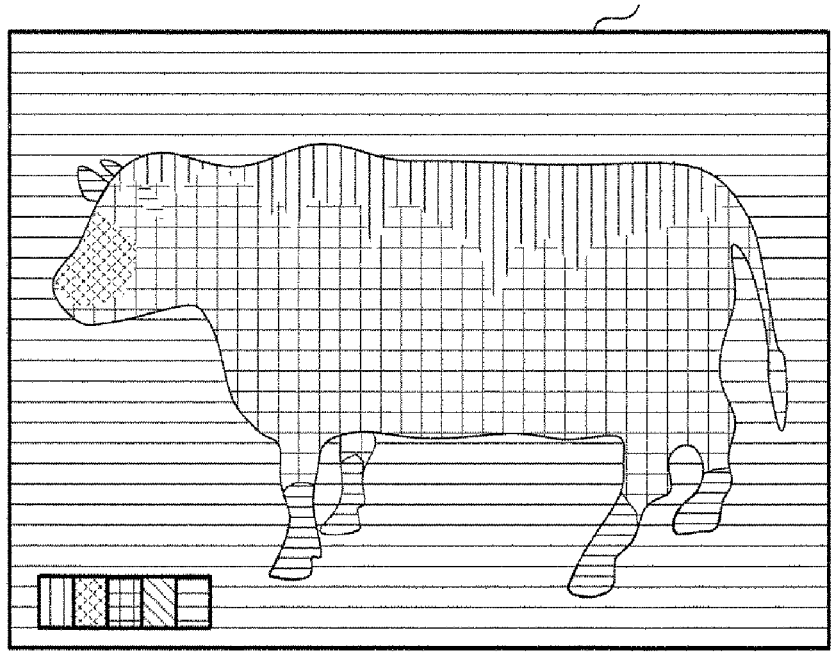

An example of an image represented by the image data acquired by the first acquiring unit 310 is shown in FIG. 4. A visible light image IM1 and an infrared image IM2 are a visible light image acquired by photographing a certain subject with the single visible light camera 201 and an infrared image acquired by photographing the certain subject with the single infrared camera 202, respectively. In FIG. 4(b), for convenience, differences in colors are represented by types of hatching.

Referring to FIG. 3 again, the second acquiring unit 350 is implemented as a communication interface and acquires from the sensor 400 environmental information indicating a living environment of cattle 500-1, 500-2, and 500-3, which are target animals to be monitored.

The storage unit 330 is a storage device implemented as one or more memories or hard disks and, upon being executed by a processor of the storage unit 330, stores a program for realizing functions of the information processing apparatus 300, which will be described below, and a database DB1 describing a plurality of reference temperatures each corresponding to a respective part of the animal. For example, this program is downloaded and installed in the information processing apparatus 300 via a communication network such as the internet.

FIG. 6 is an example of information stored in the database DB1. In this example, tables (a table for animal A and a table for animal B) in which a part and a reference temperature are associated with each other for each target animal to be monitored and a general-purpose table (a table for general use) applied regardless of a specific animal are stored in the database DB1.

The reference temperature is, for example, a temperature indicating a normal (healthy) condition. The positions and the number of parts to be registered are examples and may be appropriately determined according to the type of animal, the content to be diagnosed, and the like. The table does not need to be provided for each animal. For example, one table may be provided for all animals of one breed.

Referring to FIG. 3 again, the storage unit 330 further stores an algorithm for analyzing the visible light image and the infrared image. Installation positions (photographing viewpoints) of all the cameras included in the diagnostic system 100 are stored in the storage unit 330. Based on a positional relationship between the visible light camera 201 generating the acquired visible light image and the infrared camera 202 generating the infrared image and the photographing conditions of the visible light camera 201 and the infrared camera 202, the control unit 320 determines a correspondence between a position of a part of the subject in the visible light image data and a position of a part of the subject in the infrared image data. In other words, positions on the visible light image are mapped onto positions on the infrared image.

The control unit 320 is implemented by one or more processors and performs diagnosis of the animals based on the visible light image data and the infrared image data supplied from at least one visible light camera 201 and at least one infrared camera 202.

Selection of each of a visible light camera 201 and an infrared camera 202 whose generated image is to be used, from among the plurality of visible light cameras 201 and infrared cameras 202, can be made arbitrarily. It is not necessary to use the image data generated by a pair of a visible light camera 201 and an infrared camera 202 whose installation positions are close to each other. That is, it is sufficient to specify the correspondence between the position on the acquired visible light image and the position on the infrared image.

In detail, the control unit 320 includes a first image processing unit 321, a second image processing unit 322, and a diagnostic unit 323. The first image processing unit 321 is implemented by an image processor and performs image analysis on the visible light image supplied from the first acquiring unit 310. In detail, the first image processing unit 321 determines whether the visible light image includes the target animal to be monitored. The first image processing unit 321 then uses a predetermined pattern matching algorithm to specify an area corresponding to each of predetermined parts of an animal photographed by each visible light camera 201 in the visible light image supplied from the first acquiring unit 310.

In addition, the first image processing unit 321 may identify each of the plurality of animals photographed by the respective visible light cameras 201. For example, when a tag having a unique identification code is attached to a predefined part of each animal, the first image processing unit 321 may identify the animal by reading the identification code and referring to a database stored in the storage unit 330. Alternatively, information on a feature unique to the animal, such as a body shape, a hair pattern, a shape of a part, or the like, may be stored in the storage unit 330, and the animal may be identified by recognition of the shape or pattern from the visible light image data.

Further, the first image processing unit 321 may specify a positional relationship between a first animal and a second animal.

When one or more of predetermined parts cannot be recognized with respect to an animal photographed by a certain visible light camera 201, the control unit 320 may analyze the visible light image data acquired from all the visible light cameras 201, specify another visible light camera 201 by which the whole or a portion of the one or more parts of the animal is photographed, and further use a visible light image generated by the other visible light camera 201. That is, data of two or more visible light images are used to identify one animal. In detail, the control unit 320 refers to the DB1 to determine whether there is excess or deficiency in the specified parts, and specifies another suitable visible light camera 201 by using information about arrangement of the visible light cameras 201 if there is a part that has not been recognized. If there is no image with respect to the specified other visible light camera 201, visible light image data photographed by another visible light camera 201 may be requested by the first acquiring unit 310 so as to be transmitted.

For example, when a certain visible light camera 201 photographs an animal from the front, a part at the back of the animal's body may not be photographed. However, even in such a case, visible light image data of a visible light camera 201, which is photographed by the visible light camera 201 installed behind the animal, are used together with visible light image data obtained by the certain visible light camera 201 such that visible light image data in which images of all parts required for diagnosis of the animal can be acquired.

The second image processing unit 322 is implemented as an image processor and specifies an area in an infrared image corresponding to the area specified by the first image processing unit 321 based on an image conversion algorithm stored in the storage unit 330.

Figure 5:
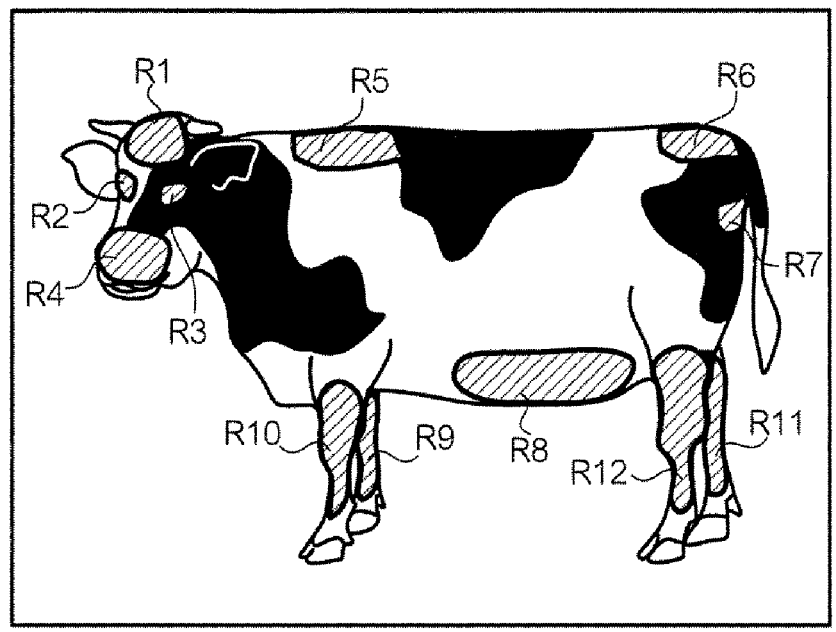
FIG. 5 shows an example of specified areas.
Figure 5:
Figure 5:
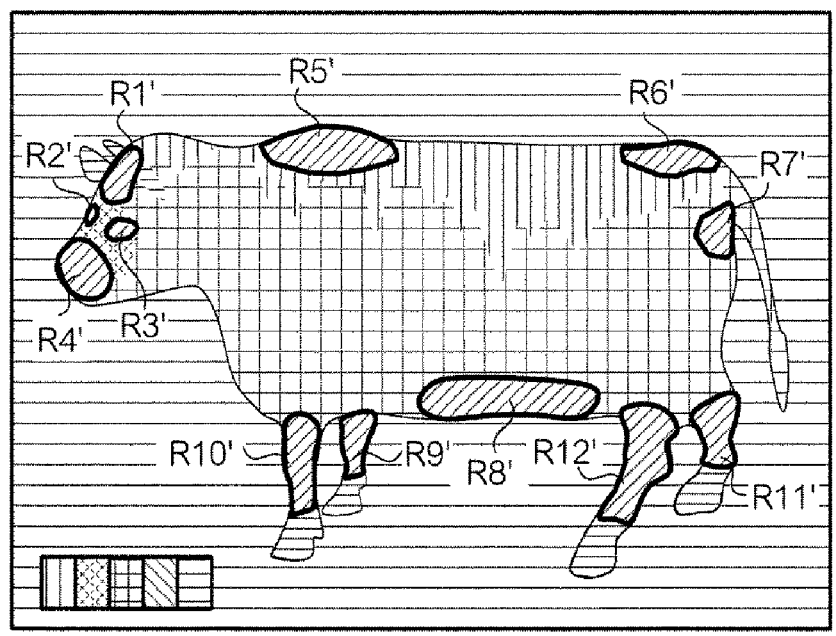

FIG. 5 shows an example of areas specified by a first image processing unit 321 and a second image processing unit 322 based on a visible light image and an infrared image of the same animal. In this example, the first image processing unit 321 specifies parts R1 to R10 on a predetermined visible light image IM1 based on the style of the analyzed outline or pattern, and specifies areas R1' to R10' on the infrared image IM2, which correspond to the specified parts R1 to R10, respectively. The first image processing unit 321 and the second image processing unit 322 may not specify an area having a finite size but may specify a coordinate of one point. That is, it is sufficient to measure a temperature at a position that is determined as a measurement target suitable for performing the diagnosis based on the temperature.

When data of a plurality of visible light images are used for one animal in the first image processing unit 321, for each visible light image, infrared image data generated by an infrared camera 202 that is provided closest to a visible light camera 201 generating the visible light image are specified and the temperature is measured for each part specified in the visible light image data.

Here, the number of visible light images and the number of infrared images from which data is obtained may not match, depending on the relationship between the installation position of the infrared camera 202 and the installation position of the visible light camera 201. That is, the temperatures at all the parts specified by one or more visible light cameras 201 for an animal may be determined based on infrared image data obtained from one or more infrared cameras 202.

The diagnostic unit 323 diagnoses the animal based on the temperature at one or more areas specified by the second image processing unit 322. In a preferred embodiment, the diagnostic unit 323 compares the temperatures at the plurality of areas specified by the second image processing unit 322 with the respective reference temperatures, and determines, based on the difference between the temperature measured for each part and the reference temperature, a condition of the animal (information about whether or not disease has developed, an age in a physiological cycle, such as the length of a period until bearing offspring or estrus, various other conditions such as mood, excitement, stress). For example, when a statistical amount such as an average value of the differences in the respective parts is equal to or more than a predetermined threshold, it is determined that the animal's condition is not healthy. Alternatively, it is determined that a predetermined symptom has developed by determining a threshold for each part and associating a symptom with one or more areas of interest. When the animals are identified by the first image processing unit 321, the diagnostic unit 323 may output a diagnosis result for each animal.

When performing a diagnosis on one animal from among a plurality of animals, the diagnostic unit 323 may refer to a measured temperature of another animal. For example, the temperature of the animal may be determined by performing statistical processing such as calculation of a mean value or a median value for measured temperature differences in all the target animals to be monitored and by correcting the measured temperature for a certain animal using the calculated value. Thus, for example, the condition of each animal can be determined by taking into consideration the characteristics of a temperature change that is commonly observed in the plurality of target animals to be monitored. For example, when an increase in body temperatures is observed in a plurality of cattle 500, it may be taken into consideration that there is a high possibility that the increase is a result of an increase in outside temperature, not a result of a symptom such as a disease, whereby a possibility of a misdiagnosis is decreased.

The diagnostic unit 323 may perform the diagnosis by adding environmental information acquired by the second acquiring unit 350 so as to improve determination accuracy on whether the temperature change is caused by the environment or by a physical condition. In detail, the reference temperature is corrected according to the air temperature, humidity, hours of sunshine, season, and the like measured by the sensor 400.

In addition, the diagnostic unit 323 may perform the diagnosis using information on a positional relationship between the animals calculated by the first image processing unit 321. For example, the first image processing unit 321 may calculate a total time or a frequency that other animals are within a predetermined distance from a target animal whose temperature is measured, and calculate a stress level in the target animal based on the calculated information. Alternatively, the first image processing unit 321 may calculate the stress level by calculating a time change (movement) of the positional relationship.

The diagnostic unit 323 may use a plurality of visible light images and a plurality of infrared images that are photographed within a predetermined period for one animal. For example, the diagnostic unit 323 may use ten pairs of visible images and infrared images that are intermittently photographed over a period of 10 seconds, and output a numerical value obtained by performing statistical processing (for example, calculation of an average value) on temperatures obtained by measuring each part ten times. As a result of this process, the possible influence of a sudden temperature fluctuation or a noise is reduced, and the measurement accuracy of the temperature is improved.

Alternatively, the temperature change may be measured for one animal over a period of from several days to several weeks, based on the fact that the diagnosis requires information on time-sequential change of the temperature in accordance with a symptom or condition of the animal. A scope of diagnosable diseases is expanded or the accuracy of diagnosis is improved, as a result of ascertaining a trend in temperature change over a long period for one animal.

The adjusting unit 340 is implemented as a processor and a communication interface generates a control signal based on information indicating the diagnosis result output by the diagnostic unit 323, and transmits the control signal to one or more environment adjusting units 600. In detail, the adjusting unit 340 determines whether to transmit the control information to each environment adjusting unit 600 and the content of control based on the information indicating the diagnosis result, and transmits a control signal indicating the determined content of control to one or more environment adjusting units 600.

Figure 7:
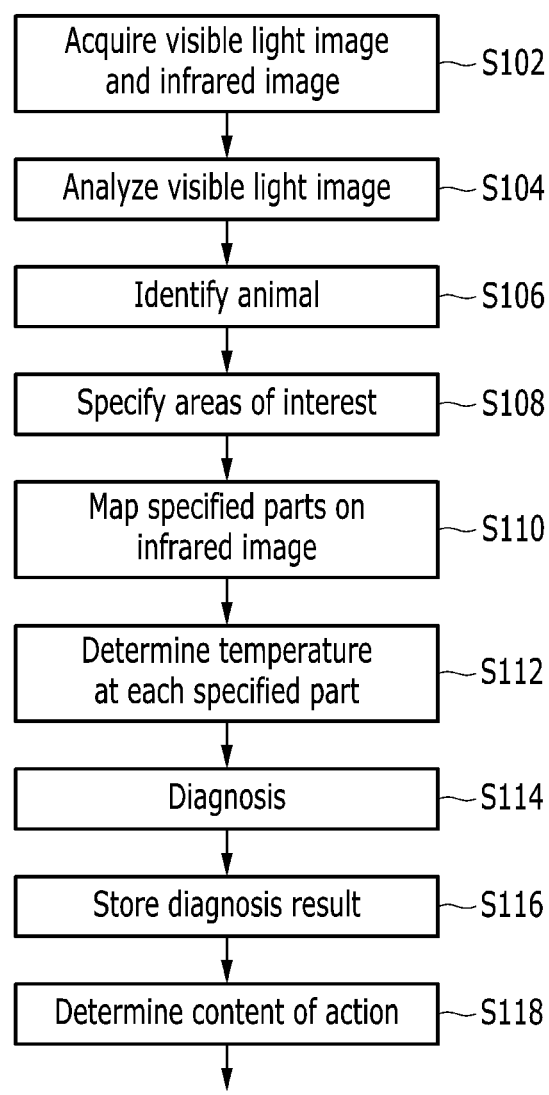
FIG. 7 shows an example of operation of a diagnostic system 100.

FIG. 7 shows an operation example of a diagnostic system 100. When a first acquiring unit 310 acquires a visible light image and an infrared image (S102), a first image processing unit 321 executes an image analysis. In detail, it is detected whether a predetermined animal has been photographed as a monitoring target (S104). If the animal has been photographed, it is identified (S106). Further, one or more predetermined areas of interest pertinent to the identified animal are specified (S108).

Subsequently, a second image processing unit 322 maps the specified parts on the infrared image (S110) and determines a temperature at each specified part based on the infrared image (S112).

Next, the diagnostic unit 323 diagnoses a subject animal based on a difference between the temperature of each specified part and a reference temperature by referring to a database DB1 (S114). The diagnostic unit 323 stores a diagnosis result in a storage unit 330 (S116) and may update the reference temperatures registered in the database DB1 if necessary. The diagnostic unit 323 then determines an action to be taken based on the diagnosis result.

In detail, the diagnostic unit 323 determines the necessity and content of control for each environment adjusting unit 600 based on the diagnosis result (S118), and transmits a control signal to one or more environment adjusting units 600 if necessary.

A series of processing steps S102 to S118, performed each time an image is acquired, may be performed according to a schedule (for example, at regular intervals) unrelated to a timing of acquisition of the image, or may be repeated until all animals that are registered as monitoring targets are detected.

In the above embodiment, it is possible to specify accurately the positions (and areas) of the predetermined parts of a subject animal by using the visible light image and to measure the temperatures at the specified areas. As a result, the measurement accuracy of temperature of the predetermined parts is improved as compared with a case where the parts are specified and the temperatures are measured only by use of thermographic imaging. Consequently, it is possible to understand more accurately the condition of the target animal to be monitored (such as whether it is healthy or sick, whether the bearing of offspring is approaching, mood, excitement, stress).

The above embodiment is only one embodiment of the present invention. To summarize, the diagnostic apparatus of the present invention may include an acquiring unit that acquires a visible light image and an infrared image photographed by a camera, a first image processing unit that specifies an area corresponding to a predetermined part of an animal photographed by the camera in the visible light image, a second image processing unit that specifies an area in the infrared image corresponding to the area specified by the first image processing unit, and a diagnostic unit that diagnoses the animal based on a temperature at the area specified by the second image processing unit.

What is claimed is:

1. A diagnostic apparatus comprising:
    a communication interface that acquires a visible light image photographed by a first camera and an infrared image photographed by a second camera; and
    one or more processors that:
        determine correspondences between positions of parts of the animal in the visible light image and positions of parts of the animals in the infrared image based on a positional relationship between the first camera and the second camera and photographing conditions of the first camera and the second camera;
        specify a first area in the visible light image corresponding to a predetermined part of an animal photographed by the first camera based on an outline or a pattern analyzed from the visible light image;
        specify a second area in the infrared image corresponding to the first area specified in the visible light image based on the correspondences; and
        diagnose the animal based on a temperature at the specified second area.

2. The diagnostic apparatus according to claim 1, further comprising a storage device that stores a plurality of reference temperatures corresponding respectively to a plurality of parts of the animal,
    wherein the one or more processors specify a plurality of areas respectively corresponding to the plurality of predetermined parts, and compare temperatures at the plurality of specified areas with each of the reference temperatures.

3. The diagnostic apparatus according to claim 1, wherein the one or more processors identify each of a plurality of animals photographed by the first camera, and output a diagnosis result for each animal.

4. The diagnostic apparatus according to claim 3, wherein the one or more processors, when diagnosing one animal from among the plurality of animals, refer to a temperature of another animal.

5. The diagnostic apparatus according to claim 3, wherein the one or more processors specify a positional relationship between the animal and other animals, and further diagnose the animal based on the positional relationship.

6. The diagnostic apparatus according to claim 1, wherein the communication interface acquires environment information indicating a living environment of the animal,
wherein the one or more processors use the environment information.

7. The diagnostic apparatus according to claim 1, wherein the visible light image and the infrared image are photographed at a plurality of points in time, and
wherein the one or more processors use a plurality of visible light images and a plurality of infrared images photographed within a predetermined period.

8. The diagnostic apparatus according to claim 1, wherein the one or more processors adjust a living environment based on a diagnosis result.

9. A method of diagnosing an animal, comprising:
determining correspondences between positions of parts of the animal in the visible light image and positions of parts of the animals in the infrared image based on a positional relationship between the first camera and the second camera and photographing conditions of the first camera and the second camera;
acquiring a visible light image photographed by a first camera and an infrared image photographed by a second camera based on an outline or a pattern analyzed from the visible light image;
specifying a first area in the visible light image corresponding to a predetermined part of an animal photographed by the first camera;
specifying a second area in the infrared image corresponding to the first area specified in the visible light image based on the correspondences; and
diagnosing the animal based on a temperature at the specified second area.

10. A non-transitory computer-readable recording medium that stores a program to be executed on a computer, the program causing the computer to execute a diagnostic method, the method comprising:
determining correspondences between positions of parts of the animal in the visible light image and positions of parts of the animals in the infrared image based on a positional relationship between the first camera and the second camera and photographing conditions of the first camera and the second camera;
acquiring a visible light image photographed by a first camera and an infrared image photographed by a second camera based on an outline or a pattern analyzed from the visible light image;
specifying a first area in the visible light image corresponding to a predetermined part of an animal photographed by the first camera;
specifying a second area in the infrared image corresponding to the first area specified in the visible light image based on the correspondences; and
diagnosing the animal based on a temperature at the specified second area.

11. The diagnostic apparatus according to claim 5, wherein the one or more processors further diagnose the animal based on the positional relationship, by calculating information on a time during which or a frequency with which the other animals are within a predetermined distance from the animal based on the positional relationship.

12. The method according to claim 9, further comprising:
specifying a positional relationship between the animal and other animals; and
further diagnosing the animal based on the positional relationship.

13. The method according to claim 12, wherein further diagnosing the animal based on the positional relationship includes calculating information on a time during which or a frequency with which the other animals are within a predetermined distance from the animal based on the positional relationship.

14. The non-transitory computer-readable recording medium according to claim 10, wherein the method further comprises:
specifying a positional relationship between the animal and other animals; and
further diagnosing the animal based on the positional relationship.

15. The non-transitory computer-readable recording medium according to claim 14, wherein further diagnosing the animal based on the positional relationship includes calculating information on a time during which or a frequency with which the other animals are within a predetermined distance from the animal based on the positional relationship.

* * * * *